(12) United States Patent
Hirt et al.

(10) Patent No.: US 10,280,140 B2
(45) Date of Patent: May 7, 2019

(54) PRODUCTION OF PYRROLIDINE DERIVATIVES

(71) Applicant: Eberhard Karls Universitaet Tuebingen Medizinische Fakultaet, Tuebingen (DE)

(72) Inventors: Bernhard Hirt, Tuebingen (DE); Claus Zeyher, Tuebingen (DE)

(73) Assignee: Eberhard Karls Universitaet Tuebingen Medizinische Fakultaet, Tuebingen (DE)

( * ) Notice: Subject to any disclaimer, the term of this patent is extended or adjusted under 35 U.S.C. 154(b) by 0 days.

(21) Appl. No.: 15/418,889

(22) Filed: Jan. 30, 2017

(65) Prior Publication Data

US 2017/0137378 A1    May 18, 2017

Related U.S. Application Data

(63) Continuation of application No. PCT/EP2015/067112, filed on Jul. 27, 2015.

(30) Foreign Application Priority Data

Jul. 30, 2014    (DE) .................. 10 2014 110 782

(51) Int. Cl.
    *C07D 207/28*    (2006.01)
(52) U.S. Cl.
    CPC .................. *C07D 207/28* (2013.01)
(58) Field of Classification Search
    CPC .................................................. C07D 207/28
    See application file for complete search history.

(56) References Cited

U.S. PATENT DOCUMENTS

| 4,652,585 | A | 3/1987 | Gerhardt et al. |
| 7,160,846 | B2 | 1/2007 | Biering et al. |
| 8,283,363 | B2 * | 10/2012 | Mack .................. C07D 207/26 514/315 |
| 2006/0257498 | A1 | 11/2006 | Stingl et al. |

FOREIGN PATENT DOCUMENTS

| DE | 3410956 A1 | 9/1985 |
| EP | 156275 A2 | 10/1985 |
| EP | 1 738 758 A1 | 1/2007 |
| EP | 1 515 755 B1 | 1/2008 |
| WO | WO-2009/038412 A2 | 3/2009 |
| WO | WO-2012/028196 A1 | 3/2012 |

OTHER PUBLICATIONS

Database Registry Online, Chemical Abstracts Service, Columbus, Ohio, Apr. 20, 1990, Database Accession No. 126646-24-0, 1 page.
Database Registry Online, Chemical Abstracts Service, Columbus, Ohio, Nov. 1, 2010, Database Accession No. 1249956-07-7, 1 page.
International Search Report and Written Opinion in International Application No. PCT/EP2015/067112, dated Oct. 2, 2015, 14 pages.
Notification of First Office Action for Chinese Application No. 201580046761.3, dated Nov. 27, 2018.
Conde et al., "*Candida antarctica* Lipase B Catalysed Amidation of Pyroglutamic Acid Derivatives. A Reaction Survey," Journal of Molecular Catalysis B: Enzymatic 7, pp. 299-306 (1999).

* cited by examiner

*Primary Examiner* — Shawquia Jackson
(74) *Attorney, Agent, or Firm* — Marshall, Gerstein & Borun LLP

(57) ABSTRACT

The present invention relates to a method for the production of a pyrrolidine derivative.

12 Claims, No Drawings

PRODUCTION OF PYRROLIDINE DERIVATIVES

CROSS-REFERENCES TO RELATED APPLICATIONS

This application is a continuation of co-pending international application PCT/EP2015/067112 filed on 27 Jul. 2015 and designating the U.S., which has been published in German, and claims priority from German patent application DE 10 2014 110 782.9 filed on 30 Jul. 2014. The entire contents of these prior applications are incorporated herein by reference.

FIELD

The present invention relates to a method for the production of a pyrrolidine derivative.

BACKGROUND

Pyrrolidine is a circular, aliphatic, secondary amine with five ring members. It is a hetero cycle. Pyrrolidine has the molecular formula $C_4H_9N$ and the CAS number 123-75-1. Derivatives of the pyrrolidine are descendants thereof which can be produced by chemical modification of pyrrolidine. Derivatives of pyrrolidine are extensively described in the state of the art.

An important pyrrolidine derivative is the so called glucoprotamin. Glucoprotamin is a substance consisting of several components. The most important components and main active substances of glucoprotamin are the (2S)-pyrrolidine-5-oxo-carboxylic acid amide, N-3-(dodecylamino)propyl and the (2S)-pyrrolidine-5-oxo-carboxylic acid amide N-3-(tetradecylamino)propyl.

Because of its anti-microbial effectivity glucoprotamin is used as a surface disinfectant, primarily in hospitals and clinics.

Glucoprotamin is obtained as a conversion product of the linear L-glutamic acid or its ester derivatives and cocospropylene-1,3-diamine. In addition to the coupling of the glutamic acid with the fatty amine mixture in the synthesis reaction a cyclization and formation of the pyrrolidine ring with dehydration takes place, which is essential for the mode of action. In addition to both of the mentioned main active sub-stances further long and short chain side products are obtained. It follows a water separation and purification of the mixture for the production of the active substances.

The currently used method for the production of glucoprotamin is described in the DE 3 410 956.

The known production method has a number of disadvantages. The known production requires for the formation of the ring closure with water binding a high reaction temperature of up to 175° C. Here the long chain alkyl group is exposed to the risk of oxidation and disintegration. The use of further derivatives, such as unsaturated fatty acids is not possible because of the oxidation processes and side reactions. For the water separation an appropriate water separator and a high vacuum are necessary which is why so far i-amyl alcohol is used as solvent and entrainer. However, this substance is harmful to health and is to be removed by means of a purification. The high reaction temperatures are not only disadvantageous in chemical terms but also increasingly unprofitable from an ecological and economical point of view. Another disadvantage of the known production process is that in the area of the pyrrolidine ring no specific predictable modifications can be introduced.

SUMMARY

Against this background it is an object underlying the invention to provide a new method for the production of pyrrolidine derivatives, such as the glucoprotamin, by means of which the before describes disadvantages can be avoided or at least reduced.

DETAILED DESCRIPTION

This object is met by a method for the production of a pyrrolidine derivative, which comprises the following steps:
1) Incubation of the reaction partners
   a) 5-oxo-pyrrolidine-2-carboxylic acid derivative with the formula I

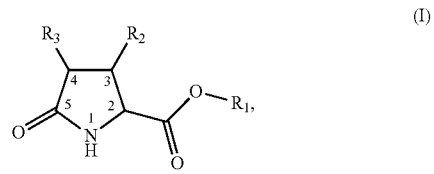

wherein
$R_1$ is a linear alkyl group with $C_1$-$C_6$;
$R_2$ and $R_3$ are independent from each other each selected from the group consisting of:

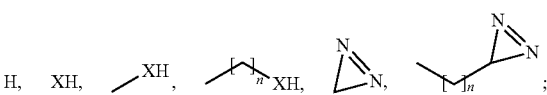

each with:
n=0- 20,
x=O or S, and b) a compound selected from the group consisting of:
   N-substituted diamine with the formula II

wherein $R_4$ is a linear alkyl or acyl with $C_2$ to $C_{22}$, and n =1 to 6, and N-substituted monoamine with the formula III

wherein $R_5$ is a linear alkyl or acyl group with $C_2$ to $C_{22}$, and

N-substituted fatty amide with the formula IV

(IV)

wherein $R_6$ is a linear alkyl group with $C_2$ to $C_{24}$, under appropriate reaction condition, and 2) isolation of the obtained pyrrolidine derivative.

As the inventors were able to find out that starting from the 5-oxo-pyrrolidine-2-carboxylic acid derivative and N-substituted mono and/or diamines and fatty amides a pyrrolidine derivative can be produced in a beneficial manner.

In contrast to the known production method the method according to the invention has a variety of advantages. The production according to the invention can already be achieved at low temperatures, for example at approximately 60° C., and only at slightly reduced pressure, at for example approximately 330 mbar. Also the length of the production process is very short and is at approximately 60 min. As a consequence, the production is faster, more gentle and more energy-efficient as in the conventional methods.

Furthermore, the production according to the invention has fewer side reactions. The purity of the reaction product is herewith increased.

In the method according to the invention no water is generated during the synthesis reaction which need to be separated in a subsequent purification in a complex manner by means of a water separator.

The gentle production method according to the invention also allows for the synthesis the use of vulnerable $C_{2-22}$-alkyl derivatives e.g. with unsaturated fatty acids. Other derivatives of active substances with another efficiency spectrum can be generated and the field of application of the pyrrolidine derivatives can be extended in that way.

Furthermore, the production method according to the invention allows for specific modifications of the starting substances which allows to modulate the kinetics of the active agent, the dynamic of the active agent, and the performance of the active agent.

A chemically complex coupling of functional groups to the starting process can be realized in advance in a separate process, so that here also the vulnerable synthesis partner of the $C_{2-22}$-alkyl derivatives is not exposed to the risk of oxidation or disintegration.

The method according to the invention also allows to specifically intro-duce functional groups which allow a coupling of the active agent e.g. to surface materials.

Finally, the method according to the invention is characterized by its low costs in contrast to the method known from the DE 3 410 956. The manufacturing processes take place at essentially lower temperatures which mean a significant reduction of the manufacturing cost.

According to the invention "pyrrolidine derivative" means a descendant of the pyrrolidine which can be obtained by chemical modification of pyrrolidine. Here the derivatives still comprise the hetero cycle of the pyrrolidine. The hetero cycle of the pyrrolidine can comprise functional groups at different positions, such as preferably at the positions 3 and 4. An example of a pyrrolidine derivative is the glucoprotamin.

According to the invention a "derivative" of 5-oxo-pyrrolidine-2-carboxylic acid encompasses a descendant thereof, which can be obtained by chemical modification thereof. The derivatives still comprise the heterocycle of the pyrrolidine, however can differ from each other in their alkyl residues. The heterocycle of the pyrrolidine can comprise functional groups at different positions, such as preferably at the positions 3 and 4. According to the invention both the S enantiomer and the R enantiomer or the racemate formed thereof are encompassed. The "5-oxo-pyrrolidine-2-carboxylic acid derivative" further encompasses a "5-oxo-pyrrolidine-2-carbon ester derivative", which is also referred to as pyroglutamate ester derivative.

According to the invention "appropriate reaction conditions" refer to such conditions which allow a chemical conversion of the reaction partners (a) and (b) to a pyrrolidine derivative. They can easily be identified by a skilled person and can be adjusted depending on the specific reaction partners.

According to a particular embodiment of the method according to the invention the 5-pyrrolidine-2-carboxyl acid derivative is modified by the coupling of at least one functional group.

This measure has the advantage that pyrrolidine derivatives with specific properties can be produced. The positions 3 and/or 4 of the pyrrolidine ring are particularly suited for a coupling.

In another embodiment of the invention the functional group coupled to the 5-oxo-pyrrolidine-2-carboxyl acid derivative is selected from the group consisting of: OH group, SH group of photoreactive group.

The attachment of for example protected hydroxyl or sulfhydryl groups to the 5-oxo-pyrrolidine-2-carboxylic acid allows the coupling of the pyrrolidine derivative to surfaces of various materials. This allows the use of the active substances as a surface coating. The attachment of photo-reactive groups results in a conditional modification of the active agent.

In another embodiment of the invention the N-substituted diamine and/or N-substituted monoamine and/or N-substituted fatty amide comprises at $R_4$ or $R_5$ or $R_6$ a mono and/or polyunsaturated alkyl and/or acyl residue.

This measure has the advantage that by choosing the chain length the characteristics of the pyrrolidine derivative can be varied in any kind.

According to a preferred embodiment of the method according to the invention the 5-oxo-pyrrolidine-2-carboxylic acid derivative is a 5-oxo-pyrrolidine-2-carboxylic acid methyl ester with the with the formula V:

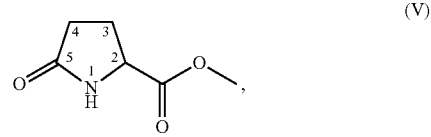
(V)

wherein it is further preferred if the N-substituted diamine is cocospropylene-1,3 diamine with the formula VI:

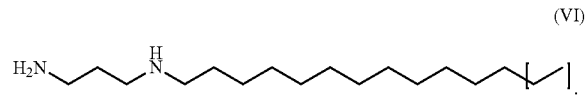
(VI)

This measure has the advantage that such reaction partners are chosen as starting substances by which a targeted production of glucoprotamin is effected. 5-oxo-pyrrolidine-2-carboxylic acid methyl ester is also referred to as L-pyroglutamic acid methyl ester. It has the molecular formula $C_6H_9NO_3$ and comprises a molecular weight of 143,14. The CAS number is 4931-66-2. Cocospropylene-1,3-diamine is also referred to as N-cocos-alkyltrimethylene diamine. With a C12 residue it has the molecular formula $C_{15}H_{34}NO_2$ and a molecular weight of 242.27, with a C14 residue it has the molecular formula $C_{17}H_{38}N_2$ and a molecular weight of 270.30. The CAS number is 61791-63-7. Cocospropylene-1,3-diamine is a product produced from natural substances and for this reason is subject to natural variations or contains further short or long chain alkyl residues.

It is preferred according to the invention if the cocospropylene-1,3-diamine comprises approximately 70 mol-% dodecylpropylenediamine and approximately 30 mol-% tetradecylpropylenediamine.

According to the finding of the inventors by this ratio especially high yields of the pyrrolidine derivative can be achieved which are at approximately 97-99% of the theoretical mass.

According to a preferred embodiment of the method according to the invention the produced pyrrolidine derivative is glucoprotamin (CAS number 164907-72-6) with the formula VII This measure has the advantage that the production is fast and thus also more gentle than with the conventional method. As the inventors were able to realize the preferred times are however sufficient to ensure a satisfying yield.

According to a preferred embodiment of the method according to the invention the incubation of the reaction partners takes place at a pressure of ≤approximately 1 bar, preferably of ≤800 mbar, further preferably of ≤approximately 500 mbar, further preferably of ≤approximately 400 mbar, and highly preferably at approximately 330 mbar.

As the inventors were able to realize a reduction of the pressure below the atmospheric pressure results in an improved yield, however the provision of a vacuum like in the state of the art is not necessary.

According to a preferred embodiment of the method according to the invention the molar ratio of the reaction partners (a) to (b) is approximately 1 to approximately 1 up to approximately 1 to approximately 2.

This measure has the advantage that according to the findings of the inventors at the indicated molar ratios especially good yields of the pyrrolidine derivative can be obtained.

According to a preferred further development of the method according to the invention the reaction side products (VIII)

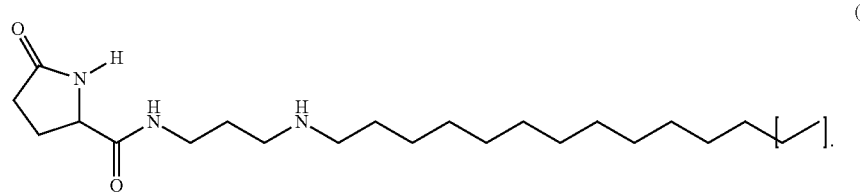

By this measure one of the most important surface disinfectants from the clinic is now producible in an advantageous manner. Glucoprotamin is also referred to as amine, N-C12-14-alcyl propylenedi-L-glutamate. In the formula the parenthesis symbolizes that there may be long or short chain alkyl residues which are present in a mixture. With a C12 residue glucoprotamin has the molecular formula $C_{20}H_{39}N_3O_2$ and the molecular weight of 353,55, with a C14 residue the molecular formula $C_{22}H_{43}N_3O_2$ and the molecular weight of 381,61. Glucoprotamin is for example marketed by the company Ecolab Germany GmbH, Düsseldorf.

According to a preferred embodiment of the method according to the invention the incubation of the reaction partners takes place at a temperature of approximately 10° C. to approximately 100° C., preferably at approximately 30° C. to approximately 90° C., highly preferably at approximately 60° C.

This measure has the advantage that a significantly lower energy input is required for the production of the pyrrolidine derivative than with the method known from the DE 3 410 956. For this reason, the production method is more gentle, more energy efficient, and more cost effective. Furthermore, the lower temperatures prevent a destruction of long chain alkyl and acyl groups. In addition, an optimum yield is ensured.

According to the invention it is preferred if the reaction partners are incubated for a duration of approximately 10 min. to approximately 100 min., further preferably of approximately 30 min. to approximately 90 min., and highly preferably for approximately 60 min.

generated in step (1) such as for example methanol, are removed, for example by distillation.

This measure has the advantage that the main active agents or the pyrrolidine derivative, respectively, is obtained in a particular pure form.

Another subject matter of the present invention relates to the use of a 5-oxo-pyrrolidine-2 carboxylic acid derivative with the formula I

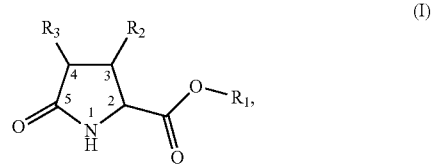

in which $R_1$ is a linear alcyl group with $C_1$-$C_6$;

$R_2$ and $R_3$ are each independent from each other selected from the group consisting of:

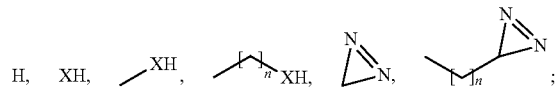

each with:

n = 0-6,

X = O or S, preferably of 5-oxo-pyrrolidine-2-carboxylic acid methyl ester with the formula V

EXAMPLES

1. The known method for the production of glucoprotamin

The previous method for the production of the 5-oxo-pyrrolidine-2-carboxylic acid derivative glucoprotamin is described in the DE 3 410 956 and schematically shown in the following.

Scheme 1: Production of glucoprotamin in the state of the art, e.g. DE 3 410 956.

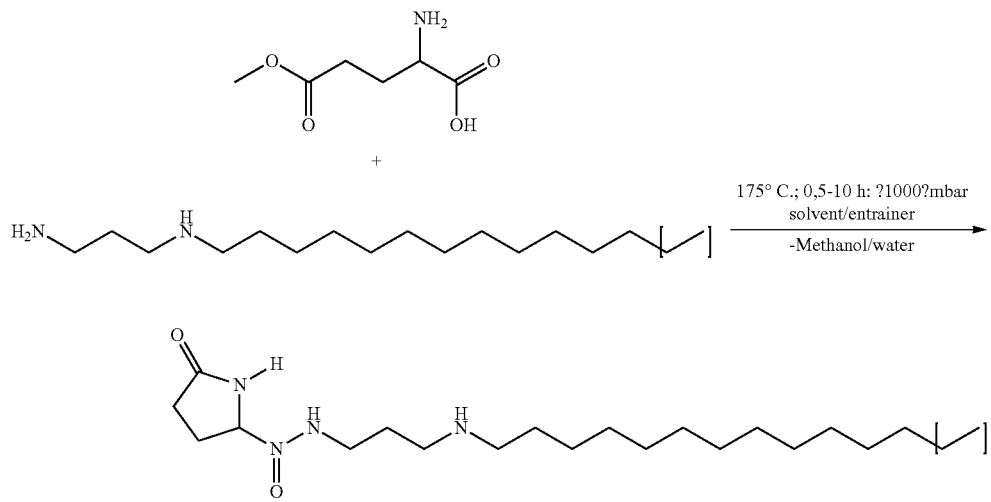

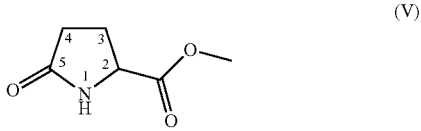

(V)

as the starting substance for the production of a pyrrolidine derivative, preferably of glucoprotamin.

The inventors have realized that for the production of pyrrolidine derivatives, such as glucoprotamin, it has not to be started from the linear substance L-glutamic acid or its ester derivatives but preferably from the 5-oxo-pyrrolidine-2-carboxylic acid derivative which is already cyclic. The synthesis reaction can then be carried out at significantly lower temperatures, higher pressure and in a shorter period of time. Further-more, the 5-oxo-pyrrolidine-2-carboxylic acid derivative can be readily modified in advance in an own process and pyrrolidine derivatives with desired properties can be produced.

The features, properties, advantages, and further developments of the method according to the invention also apply to the use according to the invention.

It goes without saying that the before-mentioned features and those to be explained in the following cannot only be used in the combination indicated in the respective case, but also in other combinations or in isolated position without departing from the scope of the invention.

The present invention is now further explained my means of embodiments which result in further properties, features and advantages. The embodiments are purely illustrative and do not restrict the scope of the invention.

In the following linear L-glutamic acid is converted with cocospropylene-1,3-diamine at high temperatures of up to 175° C. and long reaction times of up to 10 hours. Water is separated in the vacuum by means of a water separator. For this purpose i-amyl alcohol is used as a solvent and entrainer.

2. The production method according to the invention

The reaction uses the following starting substances

I. 5-oxo-pyrrolidine-2-carboxylic acid derivatives (preferably the S enantiomer, but also the R enantiomer or racemate) and II. N-substituted monoamines (2.3) and/or diamines (2.2) and/or fatty amides (2.3)

2.1 Conversion of 5-oxo-pyrrolidine-2-carboxylic acid derivatives with N-substituted monoamines Scheme 2: Conversion of the 5-oxo-pyrrolidine-2-carboxylic acid derivatives with N-substituted mono-amines

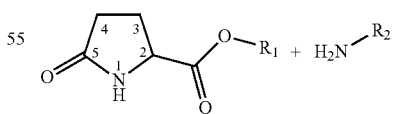

Definition of the residues:

$R_1$ = linear alkyl residues with $C_{1-6}$; preferably $C_1$;

$R_2$ = linear alkyl residue with a chain length $C_{2-22}$, wherein mono and poly unsaturated alkyl residues are included.

The reaction only requires a preferred temperature of 60° C., a preferred reaction time of 60 min., and a preferred pressure of 300-350 mbar. Methanol is distilled off.

2.2 Conversion of 5-Oxo-Pyrrolidine-2-Carboxylic Acid Derivatives with N-Substituted Diamines Scheme 3: Conversion of 5-oxo-pyrrolidine-2-carboxylic acid derivatives with N-substituted diamines

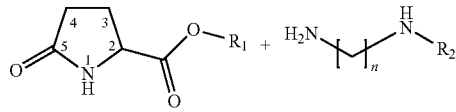

Definition of the residues:

n=1-6

$R_1$=linear alkyl residue with $C_{1-6}$; preferably $C_1$;

$R_2$=linear alkyl or acyl residue with a chain length $C_{2-22}$, wherein mono and poly unsaturated alkyl and acyl groups are included.

The reaction only requires a preferred temperature of 60° C., a preferred reaction time of 60 min., and a preferred pressure of 300-350 mbar. Methanol is distilled

2.3 Conversion of 5-Oxo-Pyrrolidine-2-Carboxylic Acid Derivatives with N-Substituted Fatty Amides Scheme 4: Conversion of 5-oxo-pyrrolidine-2-carboxylic acid derivatives with N-substituted diamines

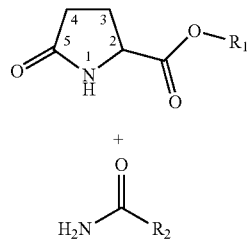

Definition of the residues:

$R_1$=linear alcyl residue with $C_{1-6}$; preferably $C_1$ $R_2$=linear alkyl residue with the chain length $C_{2-24}$, wherein mono and poly unsaturated alkyl residues are included.

The reaction only requires a preferred temperature of 60° C., a preferred reaction time of 60 min., and a preferred pressure of 300-350 mbar. Methanol is distilled off.

3. Synthesis of glucoprotamin according to the invention

3.1 General description

The two active substances subsumed under the active agent of glucoprotamin, i.e. (2S)-pyrrolidine-5-oxo-carboxylic acid amide, N-3-(dodecylamino)propyl and (2S)-pyrrolidine-5-oxo-carboxylic acid amide, N-3-(tetradecylamino)propyl, in the method according to the invention are not generated by a reaction of the linear starting substance L-glutamic acid or its ester derivatives and the fatty amine mixture dodecyl/tetradecylpropylenediamine, also referred to as cocospropylen-1,3-diamine, but by the reaction of the already cyclic starting product 5-oxo-pyrrolidine-2(S)-carboxylic acid methyl ester, which is also referred to as L-pyroglutamic acid methyl ester, with cocospropylene-1,3-diamine only at approximately 60° C., approximately 60 min., and approximately 300 to 350 mbar with a distillation off of methanol.

Scheme 5: Synthesis of glucoprotamin from 5-oxo-pyrrolidine-2(S)-carboxylic acid methyl ester and cocospropylene-1,3-diamine

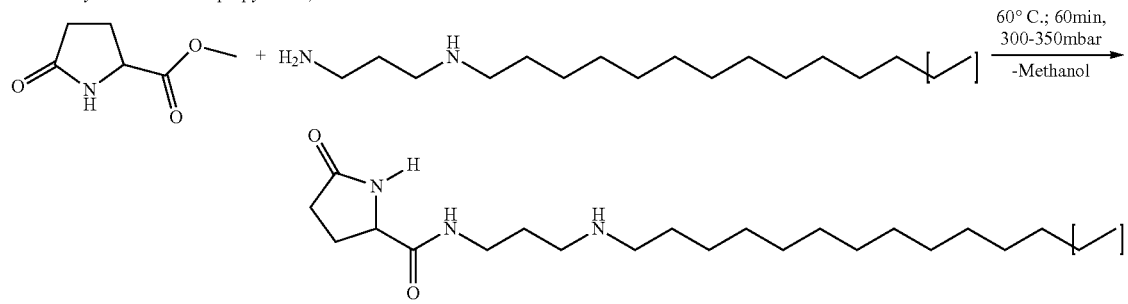

3.2 Material and Method 251 g (1 Mol) cocospropylene-1,3-diamine (CAS number 6171-63-7) (70 mol-% dodecylpropylenediamine, 30 mol-% tetradecylpropylenediamine) were melted in the water bath at 60° C. Then 143,14 g (1 Mol) 5-oxo-pyrrolidine-2(S)-carboxylic acid methyl ester were added and brought to reaction at a reduced pressure of 330 mbar in a rotary evaporator for one hour at 60° C. The methanol which was produced in the reaction (32g) was distilled off. The conversion product was liquid-viscous at 60° C. and solidifies at room temperature to a beige-yellow waxy paste. The melting temperature for the conversion product is 60-70° C.

3.3 Analysis of the Synthesis Product

The analysis of the synthesized product confirms the substance glucoprotamine glucoprotamin. The results of the high resolution mass spectrometry did result in a mass deviation of the test substance of only 0.01 to 0.04 ppm of the theoretical masses of [M+H]+=253 g/mol (2S)-pyrrolidine-5-oxo-caroboxylic acid amide, N-3-(dodecylamino)propyl and [M+H]+=286 g/mol (2S)-pyrrolidine-5-oxo-carboxylic acid amide, N-3-(tetradecylamino)propyl.

A 1H and 13C NMR structure analysis showed the compliance with the theoretically predicted spectra (Scifinder/ChemDraw 13.0).

4. Modification of the Starting Substances

Because of its mild reaction conditions, the new production method allows the use of long chain and/or unsaturated and therefore vulnerable carbon chains without running the risk of a disintegration or oxidation within the frame of the synthesis reaction. Furthermore, in the new production method already "chemically assembled" starting substances can be used in advance. Also complex chemical reactions become possible without influencing the synthesis reaction.

The starting substances 5-oxo-pyrrolidine-2-carboxylic acid derivatives and N-substituted monoamine, diamine, and fatty amide derivatives are to be modified with the objective of influencing the kinetics of the active agent, the dynamics of the active agent, and the performance of the active agent of the synthesis products.

4.1 Modification of the 5-Oxo-Pyrrolidine-2-Carboxylic Acid Derivatives

The starting substance 5-oxo-pyrrolidine-2-carboxylic acid can be modified at the positions 3 and 4 of the pyrrolidine ring. Examples will be given under 4.1.1 and 4.1.2.

4.1.1 Attachment of Groups for the Coupling to Surface Materials

The attachment e.g. of protected hydroxyl or sulfhydryl groups at the positions 3 and/or 4 of the pyrrolidine ring allows the coupling of the active agent to surfaces of various materials. This allows the use of the produced active agents as a surface coating.

Scheme 6: Modification of the 5-oxo-pyrrolidine-2-carboxylic acid derivatives by attaching of (a) hydroxyl and/or (b) sulfhydryl groups. Shown is the example of a hydroxyl group at position 4 and a sulfhydryl group at position 3. $R_1$ stands for a linear alkyl group with C1-6; preferably C1.

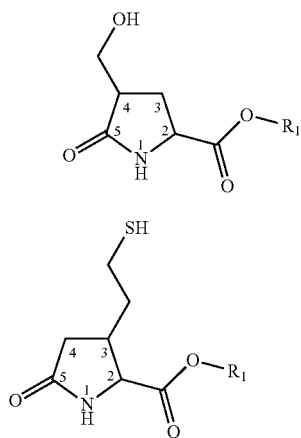

4.1.2 Attachment of Functional Groups which Allow a Modulation or a Conditioned Attachment, Activation or Inactivation of the Active Agent.

The attachment of e.g. photoreactive groups may allow a conditioned modification of the active substance.

Scheme 7: Modification of the 5-oxo-pyrrolidine-2-carboxylic acid derivative by attaching photo-reactive groups. Shown are two examples at the position 3 and position 4. R1 stands for a linear group with C1-6; preferably C1.

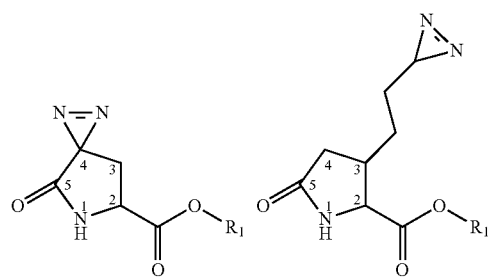

4.2 Modification of the N-Substituted Monoamine, Diamine, Fatty Amide Derivatives The mild production method according to the invention allows e.g. also the use of alkyl groups with various chain length or also in unsaturated state. A modification of the chain length can result in a changed active agent profile.

Scheme 8: representation of modified monoamine, diamine, and fatty amide groups.

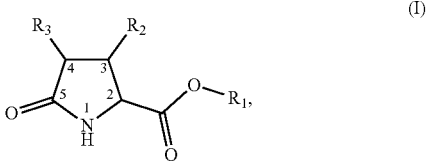

with $R_2$ =
linear alkyl residue with a chain length of $C_{2-22}$
mono and/or poly unsaturated alkyl residues
in (1) also mono and/or poly unsaturated acyl residues
n = 1-6

5. Conclusion

The inventors provide for the first time a method for the production of pyrrolidine derivatives, such as the glucoprotamin, which in comparison to the conventional method is fast, gentle, and energy efficient. The production has fewer side reactions and does not require complex purification steps. In the method according to the invention active groups can be incorporated into the pyrrolidine derivatives in a targeted manner without being destructed by the reaction conditions. In addition, the new method is particularly cost effective.

What is claimed is:

1. A method for producing a pyrrolidine derivative, which comprises the following steps:

1) Incubating (a) 5-oxo-pyrrolidine-2-carboxylic acid derivative of formula I wherein $R_1$ is a linear alkyl residue with $C_1$-$C_6$;

$R_2$ and $R_3$ are each independent from each other selected from the group consisting of:

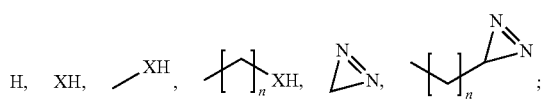

with each:
n =0- 20,
X =O or S,
and (b) a compound selected from the group consisting of:
N-substituted diamine of formula II

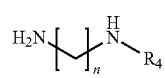

where $R_4$ is a linear alkyl or acyl residue with $C_2$ to $C_{22}$, and n =1-6; and
N-substituted monoamine of formula III

where $R_5$ is a linear alkyl or acyl residue with $C_2$ to $C_{22}$; and

N-substituted fatty amide of formula IV

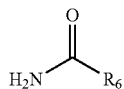

where $R_6$ is a linear alkyl group with $C_2$ to $C_{24}$;
under appropriate reaction conditions to obtain a pyrrolidine derivative, and 2) Isolating the obtained pyrrolidine derivative.

2. The method of claim 1, wherein any of the N-substituted diamine or N-substituted monoamine or N-substituted fatty amide comprises at $R_4$ or $R_5$ or $R_6$ any of a mono- or poly-unsaturated alkyl or acyl residue.

3. The method of claim 1, wherein the 5-oxo-pyrrolidine-2- carboxylic acid derivative is a 5-oxo-pyrrolidine-2-carboxylic acid methyl ester of formula V

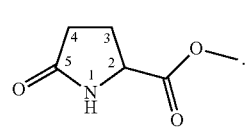

4. The method of claim 1, wherein the N-substituted diamine is cocospropylene-1,3-diamine of formula VI:

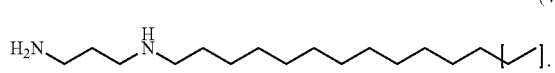

5. The method of claim 4, wherein the cocospropylene-1,3-diamine comprises approximately 70 mol-% of dodecylpropylenediamine and approximately 30 mol-% of tetradecylpropylenediamine.

6. The method of claim 1, wherein the pyrrolidine derivative is glucoprotamin of formula VII:

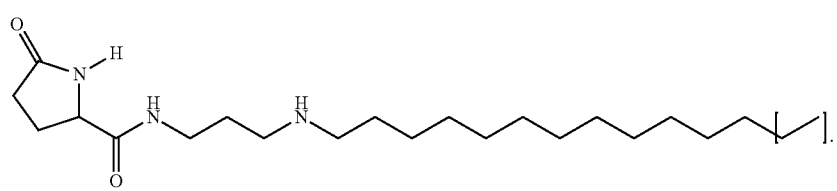

7. The method of claim 1, wherein the reaction conditions comprise an incubation temperature of approximately 60° C.

8. The method of claim 1, wherein the reaction conditions comprise an incubation time of approximately 60 min.

9. The method of claim 1, wherein the reaction conditions comprise a pressure of ≤ approximately 400 mbar.

10. The method of claim 1, wherein a molar ratio of (a) to (b) is approximately 1 to approximately 1 up to approximately 1 to approximately 2.

11. The method of claim 1, comprising removing reaction side products generated in step (1).

12. The method of claim 11, wherein the reaction side product comprises methanol and the method comprises removing the methanol by distillation.

\* \* \* \* \*